United States Patent [19]

Duffett

[11] Patent Number: Plant 5,713

[45] Date of Patent: Apr. 8, 1986

[54] CHRYSANTHEMUM PLANT NAMED GLEAM

[75] Inventor: William E. Duffett, Salinas, Calif.

[73] Assignee: Yoder Brothers, Inc., Barberton, Ohio

[21] Appl. No.: 636,856

[22] Filed: Aug. 1, 1984

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Gleam characterized as to uniqueness by the combined characteristics of pompon capitulum form; formal decorative capitulum type; yellow ray floret color; diameter across face of capitulum ranging from 5 to 7 cm. at maturity; uniform nine week flowering response; tall plant height when grown single stem; 20 to 35 cm. peduncles on open, normally terminal sprays, and 13° C. minimum temperature tolerance for initiation and development of flowering buds.

3 Drawing Figures

The present invention comprises a new and distinct cultivar, of *Chrysanthemum morifolium,* Ramat., named Gleam.

Gleam is a product of a planned breeding program which had the objective of creating new chrysanthemum cultivars having low temperature tolerance for cut spray mum programs with formal decorative capitulum type, yellow ray floret color, nine week flowering response, and the ability to produce commercially acceptable quality in year round programs. Such traits in combination were not present or needed improvement in previously available commercial cultivars.

Gleam, identified as 81719004, was originated from a cross made by William E. Duffett in a controlled breeding program in Salinas, Calif. in 1980. The female parent, identified as 78768001, was Brass. The male parent, identified as 781030004, was an unnamed seedling.

Gleam was discovered and selected as one flowering plant within the progeny of the stated cross by William E. Duffett on Nov. 6, 1981 in a controlled environment in Bogota, Colombia.

The first act of asexual reproduction of Gleam was accomplished when vegetative cuttings were taken from the initial selection in January 1982 in a controlled environment in Bogota, Colombia by a technician working under formulations established and supervised by William E. Duffett through Fernando Jaramillo.

Horticultural examination of selected units initiated Mar. 30, 1983 has demonstrated that the combination of characteristics as herein disclosed for Gleam are firmly fixed and are retained through successive generations of asexual reproduction.

Gleam has not been observed under all possible environmental conditions. The phenotype may vary significantly with variations in environment such as temperature, light intensity, and day length. The following observations, measurements and comparisons describe plants grown in Bogota, Colombia under greenhouse conditions which approximate those generally used there in commercial practice.

The following traits have been repeatedly observed and are determined to be basic characteristics of Gleam which in combination distinguish this chrysanthemum as a new and distinct cultivar:

1. Pompon capitulum form.
2. Formal decorative capitulum type.

3. Yellow ray floret color.
4. Diameter across face of capitulum ranging from 5 to 7 cm. at maturity.
5. Uniform nine week photoperiodic flowering response to short days.
6. Long peduncle length, ranging from 20 to 35 cm.
7. Tall plant height, requiring one long day week prior to short days to attain a flowered plant height of 100 to 110 cm. for year around flowering.
8. Low temperature tolerance of 13° C. for initiation and development when grown in single stem cut spray programs with a continuous dark period of 12 hours.

The accompanying photographic drawings show typical inflorescence and leaf characteristics of Gleam, with the colors being as nearly true as possible with illustrations of this type. Sheet 1 is a color photograph of Gleam grown as a single stem cut spray. Sheet 2 is a black and white photograph of three views of the inflorescence of Gleam. Sheet 3 is a black and white photograph showing the upper surface and under surface of leaves of Gleam at three stages of development (mature, intermediate and immature).

Of the many commercial cultivars known to the present inventor, the most similar in comparison to Gleam is Yellow Polaris. Reference is made to attached Chart A which compares certain characteristics of Gleam to those same characteristics of Yellow Polaris. Gleam develops deeper flower color, more formal decorative type, smaller diameter of capitulum, taller plant height and faster response to 12 hour day photoperiods. The peduncle length and tolerance of 13° C. temperature for bud initiation and development for Gleam are similar to those same characteristics of Yellow Polaris.

In the following description, color references are made to The Royal Horticultural Society Colour Chart. The color values were determined between 11:30 A.M. and 11:45 A.M. on Dec. 27, 1983 under 380 foot-candle light intensity at Salinas, Calif.

Classification:

*Botanical.*—*Chrysanthemum morifolium,* Ramat., cv Gleam.

*Commercial.*—Decorative cut spray mum.

I. Inflorescence:

A. *Capitulum.*—Form: Pompon. Type: Formal decorative. Diameter Across Face: 5 to 7 cm.

B. *Corolla of ray florets.*—Color (General Tonality From a Distance of Three Meters): Yellow. Color (upper surface): 6A, 6B. Color (under surface): 6C. Shape: Short, oval; a few are tubular.

C. *Corolla of disc florets.*—Color (mature): 1A. Color (immature): 154A.

D. *Reproductive organs.*—Androecium: Present disc florets only; scant pollen. Gynoecium: Present both ray and disc florets.

II. Plant:

A. *General appearance.*—Height: Tall; 100 to 110 cm. as a flowering plant from a rooted cutting, with seven long days for year around flowering maintaining a minimum nightly 12 hour continuous dark period.

B. *Foliage.*—Color (upper surface): 137A. Color (under surface): 147C. Shape: Deeply lobed and sharply serrated.

CHART A

COMPARISON OF GLEAM AND YELLOW POLARIS

| CULTIVAR | RAY FLORET COLOR | CAPITULUM FORM AND TYPE |
|---|---|---|
| GLEAM | YELLOW | POMPON FORMAL DECORATIVE |
| YELLOW POLARIS | YELLOW | FLAT DECORATIVE |

CHART A-continued

COMPARISON OF GLEAM AND YELLOW POLARIS

| CULTIVAR | SPRAY FORMATION | DIAMETER ACROSS FACE OF CAPITULUM |
|---|---|---|
| GLEAM | 20 to 35 cm. PEDUNCLES | 5 to 7 cm. |
| YELLOW POLARIS | 20 to 25 cm. PEDUNCLES | 8 to 9 cm. |

| CULTIVAR | PLANT HEIGHT | FLOWERING RESPONSE PERIOD | LOW TEMPERATURE TOLERANCE |
|---|---|---|---|
| GLEAM | TALL 100 to 110 cm. | 9 WEEKS | 13° C. |
| YELLOW POLARIS | TALL 90 to 100 cm. | 11 WEEKS | 13° C. |

COMPARISONS MADE OF PLANTS GROWN AS SINGLE STEM CUT SPRAY MUMS WITH 7 LONG DAYS IN BOGOTA, COLOMBIA

I claim:

1. A new and distinct plant of *Chrysanthemum morifolium,* Ramat., named Gleam, as described and illustrated, and particularly characterized as to uniqueness by the combined characteristics of pompon capitulum form; formal decorative capitulum type; yellow ray floret color; diameter across face of capitulum ranging from 5 to 7 cm. at maturity; uniform nine week flowering response; tall plant height when grown single stem; 20 to 35 cm. peduncles on open, normally terminal sprays; and 13° C. minimum temperature tolerance for initiation and development of flowering buds.

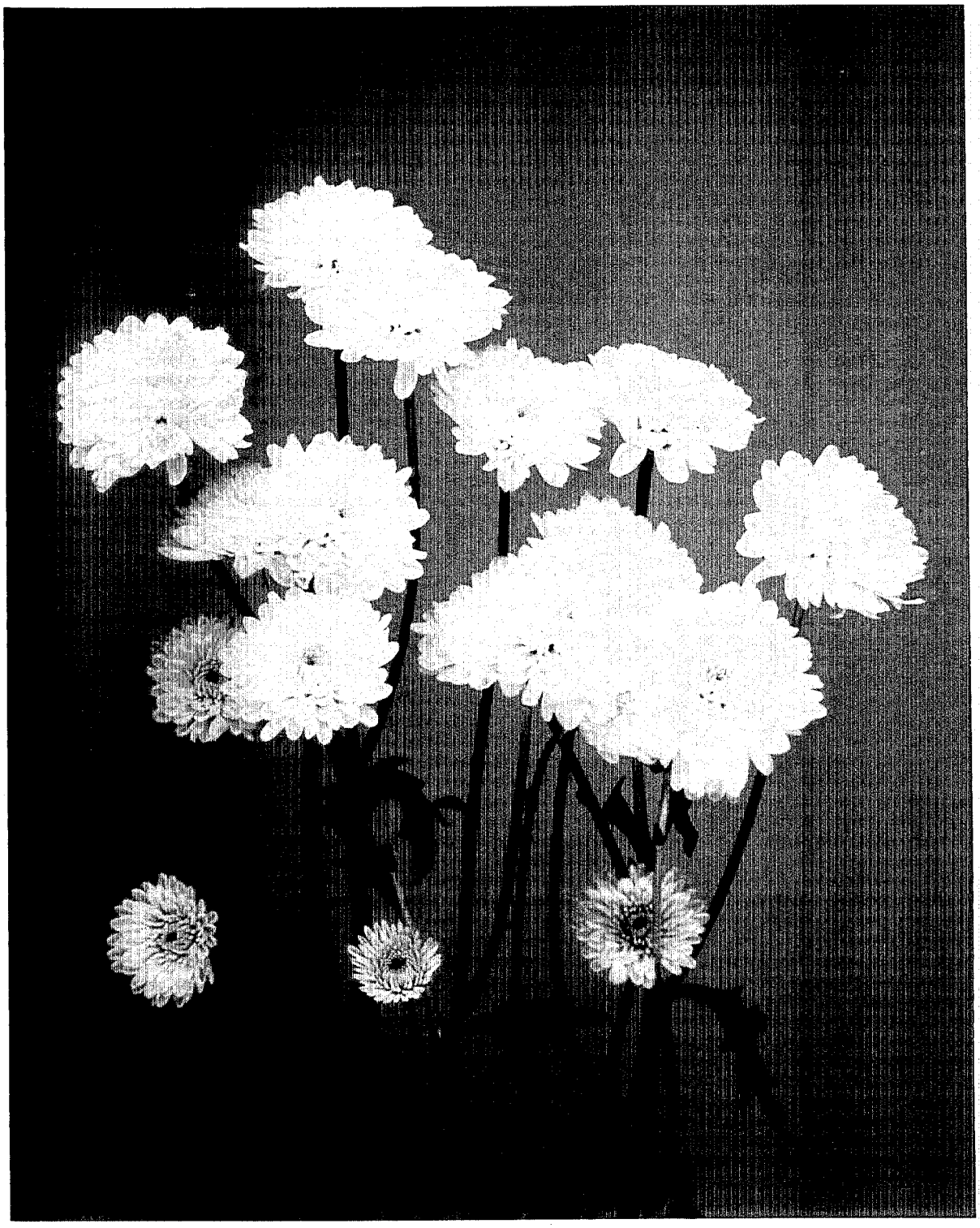

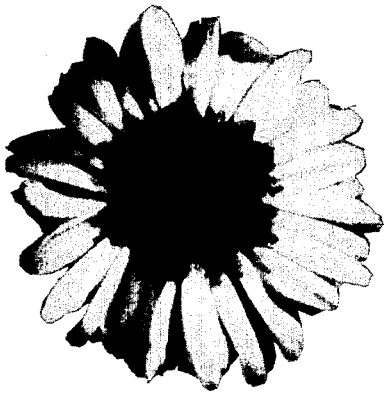
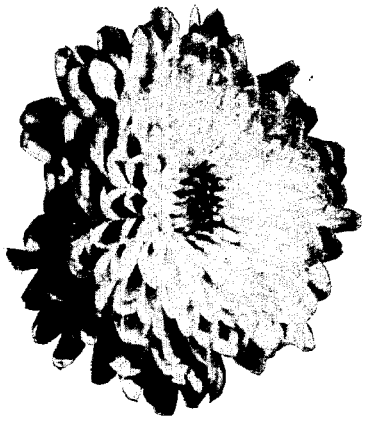
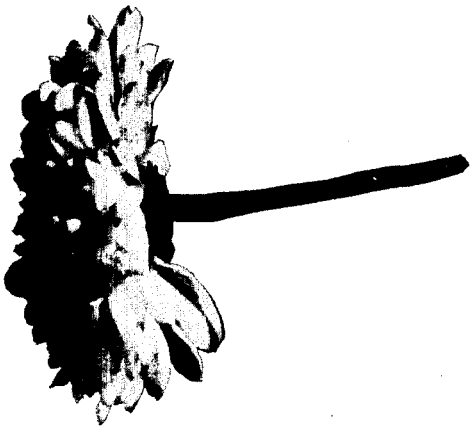

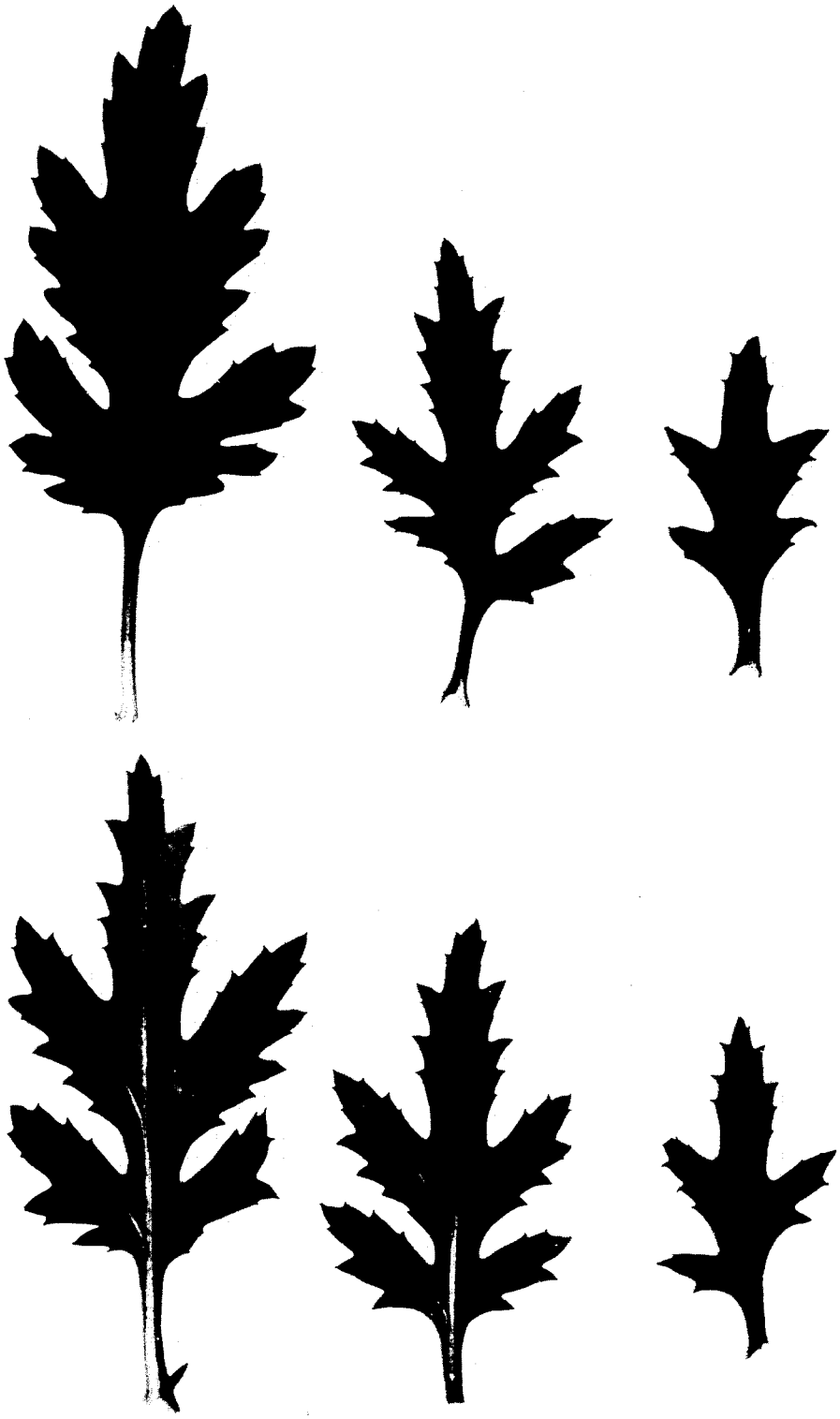

* * * * *